United States Patent
Monty et al.

(10) Patent No.: US 10,219,738 B2
(45) Date of Patent: Mar. 5, 2019

(54) SYSTEM AND METHOD FOR IMAGING IN LASER DENTAL TREATMENT

(71) Applicant: Convergent Dental, Inc., Natick, MA (US)

(72) Inventors: Nathan P. Monty, Shrewsbury, MA (US); Charles H. Dresser, Bethel, ME (US)

(73) Assignee: Convergent Dental, Inc., Needham, MA (US)

( * ) Notice: Subject to any disclaimer, the term of this patent is extended or adjusted under 35 U.S.C. 154(b) by 324 days.

(21) Appl. No.: 14/213,363

(22) Filed: Mar. 14, 2014

(65) Prior Publication Data

US 2014/0272775 A1   Sep. 18, 2014

Related U.S. Application Data

(60) Provisional application No. 61/793,117, filed on Mar. 15, 2013.

(51) Int. Cl.
*A61B 5/00* (2006.01)
*A61C 9/00* (2006.01)
*A61C 1/00* (2006.01)
*A61B 5/107* (2006.01)

(52) U.S. Cl.
CPC .......... *A61B 5/4547* (2013.01); *A61B 5/0088* (2013.01); *A61C 1/0046* (2013.01);
(Continued)

(58) Field of Classification Search
CPC .. A61B 5/0088; A61B 5/4547; A61N 5/0613; A61N 2005/067; A61C 9/0053; A61C 1/0046
(Continued)

(56) References Cited

U.S. PATENT DOCUMENTS

| 5,645,550 A * | 7/1997 | Hohla ............... A61B 18/20 606/1 |
| 2004/0097910 A1* | 5/2004 | Brugger ............ A61B 18/201 606/10 |

(Continued)

FOREIGN PATENT DOCUMENTS

| EP | 2213223 A1 | 8/2010 | |
| EP | 2520221 A1 * | 11/2012 | ............... A61B 1/24 |

(Continued)

OTHER PUBLICATIONS

International Search Report and Written Opinion for International Patent Application No. PCT/US2014/028844 dated Aug. 8, 2014 (11 pages).

(Continued)

*Primary Examiner* — Matthew Nelson
(74) *Attorney, Agent, or Firm* — Goodwin Procter LLP (57) ABSTRACT

A device for determining a contour of a dental treatment area during treatment thereof includes a laser beam guidance system and an imaging system. The laser beam guidance system can guide a laser beam and, optionally, a scanning light to a dental treatment area, and the imaging system, which can include an adjustable focus image sensor, can obtain an image of the dental treatment area based on light rays reflected therefrom. The device also includes a computation system to compute a contour, e.g., a 2D contour, of a surface of the dental treatment area based on the image obtained by the imaging system and, optionally, geometries of one or more components of the laser beam guidance system and/or optical components associated with the imaging system.

26 Claims, 7 Drawing Sheets

(52) U.S. Cl.
CPC ............ *A61C 9/006* (2013.01); *A61C 9/0066* (2013.01); *A61B 5/1079* (2013.01); *A61B 2576/02* (2013.01)

(58) Field of Classification Search
USPC .................... 433/27–29; 607/89, 88; 604/20
See application file for complete search history.

(56) References Cited

U.S. PATENT DOCUMENTS

| | | | | |
|---|---|---|---|---|
| 2004/0254476 | A1* | 12/2004 | Quadling | A61B 5/0066 600/476 |
| 2010/0189341 | A1* | 7/2010 | Oota | A61B 1/0019 382/154 |
| 2012/0015318 | A1 | 1/2012 | Kasenbacher | |
| 2012/0202167 | A1* | 8/2012 | Kasenbacher | A61B 18/20 433/29 |
| 2013/0059264 | A1* | 3/2013 | Monty | A61C 1/0046 433/29 |

FOREIGN PATENT DOCUMENTS

| | | |
|---|---|---|
| JP | 2001-510357 A | 7/2001 |
| JP | 2006-525066 A | 11/2006 |
| JP | 2010-194296 A | 9/2010 |
| JP | 2012-502673 A | 2/2012 |
| WO | WO-2012/083967 A1 | 6/2012 |

OTHER PUBLICATIONS

Notice for Reason of Rejection dated Dec. 21, 2017 for Japanese Application No. 2016-502921.

European Office Action dated Nov. 23, 2017 for European Patent application No. 14723928.9.

Japanese Office Action dated Jul. 2, 2018 for application No. 2016-502921.

* cited by examiner

SYSTEM AND METHOD FOR IMAGING IN LASER DENTAL TREATMENT

CROSS-REFERENCE TO RELATED APPLICATIONS

This application claims benefit of priority to U.S. Provisional Patent Application No. 61/793,117, entitled "System and Method for Imaging in Laser Dental Treatment," filed on Mar. 15, 2013, the disclosure of which is incorporated herein by reference in its entirety.

TECHNICAL FIELD

The present invention generally relates to three dimensional (3D) scanning and, in particular, to generating a model of unevenly shaped objects such as dental structures.

BACKGROUND

In dentistry, 3D scanning and imaging are rapidly replacing older techniques that use castings and impression materials. Scanning is typically fast relative to the older methods, can instantly provide a digital file, and can eliminate substantially all shrinkage and handling issues associated with castings and impressions. Additionally, the digital images can be easily transmitted to a dental laboratory or dental computerized numerical control (CNC) milling machine, for generating a suitable dental restoration component such as a dental crown.

Scanners, in general, are devices for capturing and recording information from the surface of an object. The use of scanners to determine a 3D surface contour of an object, e.g., to create a 3D model thereof, using non-contact optical methods is important in many applications including in vivo scanning of dental structures. Typically, a 3D surface contour is formed from a collection of points (often called a cloud of points) where, at a particular time, the relative position of each point in the collection/cloud represents an approximate contour of the scanned object's surface.

In these optical methods, a common principle underlying contour measurement using the collection of point position data is triangulation. Given one or more triangles where the baseline of each triangle includes two optical centers and the vertex of each triangle is a particular point on or near a target object surface, the range of that particular point on or near the target object surface from each of the optical centers can be determined based on the optical separation and the angle of light transmitted from and/or received at the optical centers to/from the particular point. If the coordinate positions of the optical centers in a specified coordinate reference frame (e.g., a Cartesian X, Y, Z reference frame), are known, the relative X, Y, Z coordinate position of the vertex, i.e., the point on or near the target surface, can be computed in the same reference frame. Typically, the light rays from an illumination source to a point on the target form one leg, i.e., edge, of the triangle, and the rays reflected from the target point to an image sensor form the other leg, i.e., edge, of the triangle. In a system using a single image sensor, the angle between the two legs can be determined because the positions of the illumination source and the sensor and the angle at which a beam of illumination light is directed to the surface to be scanned are known. Using these known parameters and the computed angle of reflection, the expected position of the point of reflection on the surface to be contoured can be determined. By repeating this procedure to determine the respective positions of a number of points of reflection a curvature of the reflection surface, i.e., the 3D contour thereof, can be determined.

Triangulation methods can be divided into passive triangulation and active triangulation. Passive triangulation (also known as stereo analysis) typically utilizes ambient light and the two optical centers along the baseline of the triangle include two cameras/image sensors. In two sensor passive systems, knowledge of the angle of illumination light incident upon the object to be scanned is not required. In contrast, active triangulation typically uses one camera as one optical center of the triangle along the baseline and, instead of a second camera at the other optical center, active triangulation uses a source of controlled illumination (also known as structured light). One optical center is a source of light and the other optical center is the imaging device, as described above.

Stereo/passive analysis, while conceptually straightforward, is not widely used, e.g., due to the difficulty in obtaining correspondence between features observed in different camera images. The surface contour of objects with well-defined edges and corners, such as blocks, can be relatively easy to measure using stereo analysis. Objects that have smoothly varying surfaces, such as skin, tooth surfaces, etc., have relatively fewer easily identifiable points of interest, such as corners, edge points, etc. This can present a significant challenge to the stereo analysis techniques. Active triangulation is therefore often preferred in generating 3D contours of such objects having smoothly varying surfaces.

Active triangulation, or structured light methods, can overcome or at least minimize the stereo correspondence problems by projecting one or more known patterns of light onto an object to determine the shape thereof. An example structured light is a spot of light, typically produced by a laser. Accuracy of contour determination can be increased by moving a fine spot in a specified pattern, e.g., along a line, in a zig-zag pattern, and/or a spiral pattern. One large spot can also be used, however. The geometry of the setup of the light projector and the camera observing the spot of light reflected from a surface of the target object can enable, e.g., via trigonometric calculations, the determination of a range of the point from which the light spot is reflected from one or both optical centers (i.e., the light projector and camera), as described above. Light projection patterns such as a stripe or two-dimensional patterns such as a grid of light dots can be used to decrease the time required to capture and/or analyze the images of the target surface.

The resolution of the measurement of the surface of a target object using structured light generally depends on the fineness of the light pattern used and the resolution of the camera used to observe the reflected light. Typically, the overall accuracy of a 3D laser triangulation scanning system is based on the ability thereof to meet two objectives, namely: (i) accurately measuring the center of the illumination light reflected from the target surface, and (ii) accurately measuring the position of the illumination source and the camera at each of the positions used by the scanner to acquire an image.

Commercially available 3D scanner systems have been developed for the dental market that accommodate the variety of human dentitions by incorporating an operator held, wand type scanner. In these systems, the operator typically moves the scanner over the area to be scanned and collects a series of image frames. In this case, however, a positional correspondence between image frames is typically not maintained; instead each frame is captured from an unknown coordinate position that is independent of the position and orientation of the wand at the instant the previous one or more frames of images were captured. In addition, all orientation information about the illumination sources and imaging devices and references thereto from scanning prior to treatment are generally not available to a scan after the treatment, because the scanner cannot be continuously located in the mouth during treatment with other instrumentation used for treatment.

These handheld systems must therefore rely on scene registration or the application of an accurate set of fiducials over the area to be scanned. But, for 3D structures such as teeth, the use of pattern recognition or fiducials for frame registration can be error prone, because tooth surfaces do not always provide sufficient registration features to allow for high accuracy scene registration. Accurate placement of fiducials to a resolution that is often required is generally impractical over the size of a typical tooth.

Another 3D measurement method includes auto-focus depth measurement with image recognition. With a short depth of field, the camera is focused at predefined depth (e.g., Z1), and an image is captured. The image is then processed, e.g., using an image recognition software, so that the "in-focus" sections of the image can be determined. Another image is then captured at a second predefined depth (e.g., Z2), and the "in-focus" sections in the second image are identified. The Z depth positioning, image capture, and image recognition are repeated according to a required resolution. Once all of the images are captured, the individual image slices can be stacked together to create a 3D image of the object.

In connection with scanning and modeling a treatment area, this method often produces 3D scans lacking the required level of accuracy. This is largely because the images are captured before and after the treatment only, and no images are captured during treatment because that requires interchanging treatment and imaging devices, which cause delay in treatment, inconvenience to the patient, and may also pose safety risk to all those involved in the treatment, particularly when lasers are used in the treatment. Therefore, improved systems and methods are need for scanning areas/regions to be treated.

SUMMARY OF THE INVENTION

In order to improve the quality of conventional 3D measurement during hard tissue cutting, various embodiments of a laser cutting system integrate an optical scanning and measurement system and a laser-based ablation system. The scanner can include an active triangulation measurement technology, or in-focus image recognition technology, or both. Unlike the conventional systems, however, various embodiments of the integrated system enable reconstruction of a 3D image of the removed tissue using a number of essentially two-dimensional (2D) images and 2D contours based on those 2D images. The 2D images and contours can correspond to thin slices of the tissue, i.e., a slice thickness can be, for example, about 0.02 mm, 0.05 mm, 0.1 mm, 0.5 mm, etc. Various 2D images and the contours generated therefrom correspond to images taken during treatment, so as to provide an accurate 3D model of the tissue that is removed during treatment.

Conventional scanners and laser-based treatment systems typically include optical components that are not compatible with each other. As such, these two types of systems cannot be readily combined. To facilitate integration of a scanning system and a treatment system, in various embodiments at least some components of the optical subsystem for laser delivery (also called a beam-guidance subsystem) are adapted to perform at least some of the scanning/measurement functions, as well. Additionally, or in the alternative, some components of the scanning/measurement system may be positioned at selected locations and orientations relative to the components of the beam-guidance system such that the combined geometries of the two subsystems can be used in the computation of surface contours, while minimizing any interference of the components of the scanning system with the delivery of the laser beam.

Accordingly, in one aspect, a device for determining a contour of a dental treatment area includes a laser beam guidance system and at least one imaging system. The laser beam guidance system can guide a laser beam via a hand piece to a dental treatment area. The imaging system can obtain an image of the dental treatment area based on light rays reflected therefrom and traveling via the hand piece. The device also includes a computation system adapted for determining, based on the image obtained by the imaging system, a contour of a surface of the dental treatment area. The computations may be based on geometries of one or more components of the laser beam guidance system and/or optical components associated with the imaging system. The device may include two or more imaging systems.

In some embodiments, the imaging system includes an adjustable focus lens. The device may also include a joystick and/or a foot pedal for adjusting a focal length of the adjustable focus lens. The adjustable focus lens may include one or more of a motorized lens stack and a liquid lens. The imaging system in its entirety or some components thereof may be located within the hand piece. The computation system may be adapted for determining an in-focus portion of the image. Alternatively, the computation system may be adapted for determining the contour based at least in part on a geometry of a component of the laser beam guidance system and/or a geometry of a component of the imaging system.

In some embodiments, both the laser beam and the light rays reflected from the dental treatment area, that are received by an imaging system, travel along a common optical axis. The device may include a splitter for directing the light rays reflected from the dental treatment area to the imaging system, instead of directing such rays to the laser source. In some embodiments, the laser beam is guided to the dental treatment area along a first axis and light rays reflected from the dental treatment area, that are received by an imaging system, travel along a second axis that is at an angle with respect to the first axis. The device may include two or more imaging systems. One imaging system may receive light traveling along the common optical axis and another imaging system may receive light traveling along the second axis. In some embodiments, one imaging system may receive light traveling along the second axis and another imaging system may receive light traveling along a different, third axis, that is also at an angle relative to the first axis.

The device may include an illumination system for providing light to the dental treatment area. The illumination system may be adapted for providing light having a pattern, and the pattern may include one or more of a spot, a one-dimensional pattern, and a two-dimensional pattern. In some embodiments, the laser beam guidance system is adapted to scan the dental treatment area by directing light from the illumination system, e.g., according to a specified pattern and/or with a specified shape.

In another aspect, a method of determining a contour of a dental treatment area includes (a) receiving at an imaging system a first image based on a first set of light rays reflected from a dental treatment area and traveling via a hand piece, and (b) generating a first contour of the dental treatment area based on the first image. The method also includes (c) directing via the hand piece a laser beam to the dental treatment area, e.g., using a laser beam guidance system. At least a portion of tissue from the dental treatment area may be removed as a result of directing the laser beam. The method further includes (d) receiving at the imaging system a second image based on a second set of light rays reflected from the dental treatment area and traveling via the hand piece, and (e) generating a second contour of the dental treatment area based on the second image. The steps (c) through (e) may be repeated, alternating between imaging and ablation, until treatment is completed. The first contour and/or the second contour may include a two-dimensional (2D) contour.

In some embodiments, receiving the first image includes adjusting a focal length associated with the imaging system, and generating the first contour includes determining an in-focus portion of the first image. The focal length may be adjusted using a joy stick and/or a foot pedal. In some embodiments, both the laser beam and the first and second sets of light rays reflected from the dental treatment area and received by the imaging system travel along a common optical axis.

In some embodiments, receiving the first image includes scanning the dental treatment area according to a pattern of light obtained from an illumination system. The laser beam may be guided to the dental treatment area along a first axis and the first and second sets of light rays reflected from the dental treatment area and received by the imaging system may travel along a second axis that is at an angle with respect to the first axis. The pattern of the illumination light may include a spot, a one-dimensional pattern, and/or a two-dimensional pattern. In some embodiments, the laser beam guidance system is controlled so as to scan the dental treatment area according to the pattern of light.

In some embodiments, the method included using the 2D contours to generate a three dimensional (3D) model of portions of tissue removed from the dental treatment area. The method may further include creating a restoration using the 3D model. As the 2D contours are determined from tissue scans that are interleaved between different treatment steps, and because the system can estimate the depth of tissue removed in each of those treatment steps according to the system parameters, the reconstruction of the 3D model can be based on the estimated depth corresponding to each one of the 2D contours, thereby increasing the accuracy of the 3D model. The 3D model may be modified prior to creating the restoration. The method may also include applying the restoration to the dental treatment area.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals generally refer to the same or similar elements. In different drawings, the same or similar elements may be referenced using different reference numerals. The drawings are not necessarily to scale, emphasis instead being placed upon illustrating aspects of the invention. In the drawings.

DETAILED DESCRIPTION

Figure 1:
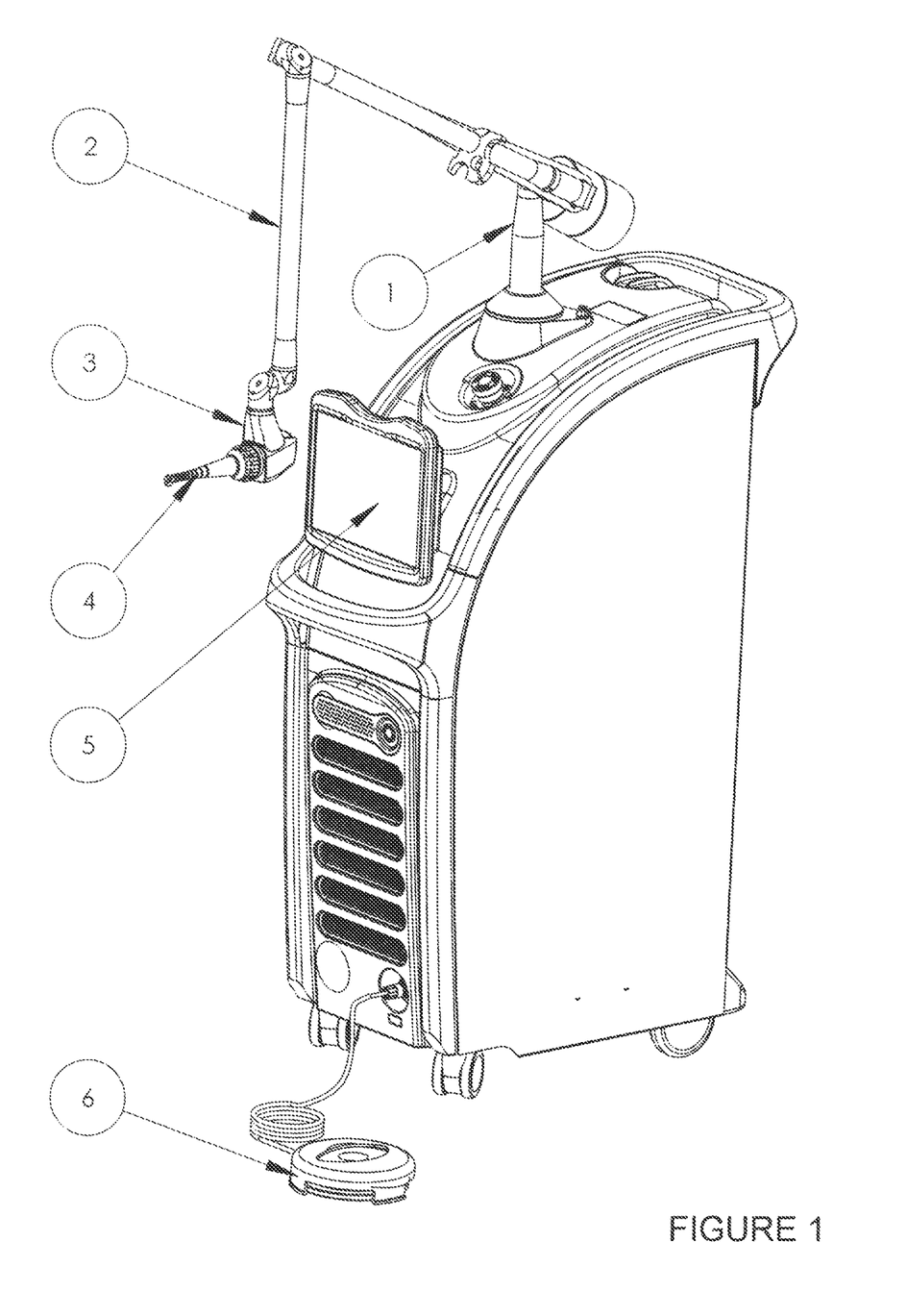
FIG. 1 depicts an overall laser-based system adapted for both treatment and scanning the area to be treated, according to one embodiment.

With reference to FIG. 1, a laser source can direct a laser beam into an articulating arm launch 1. The beam may be further directed within an articulated arm 2, and may exit therefrom at the end opposite the launch. In this laser-based dental treatment system, a main chamber 3 is connected to an interchangeable hand piece 4. One embodiment includes a variable speed foot pedal 6 to control the laser source and/or various parameters of the dental system. A user interface (e.g., a touch screen input device) and/or monitor 5 can display images, and may be used to control various system parameters instead of or in addition to the foot pedal 6.

Figure 2A:
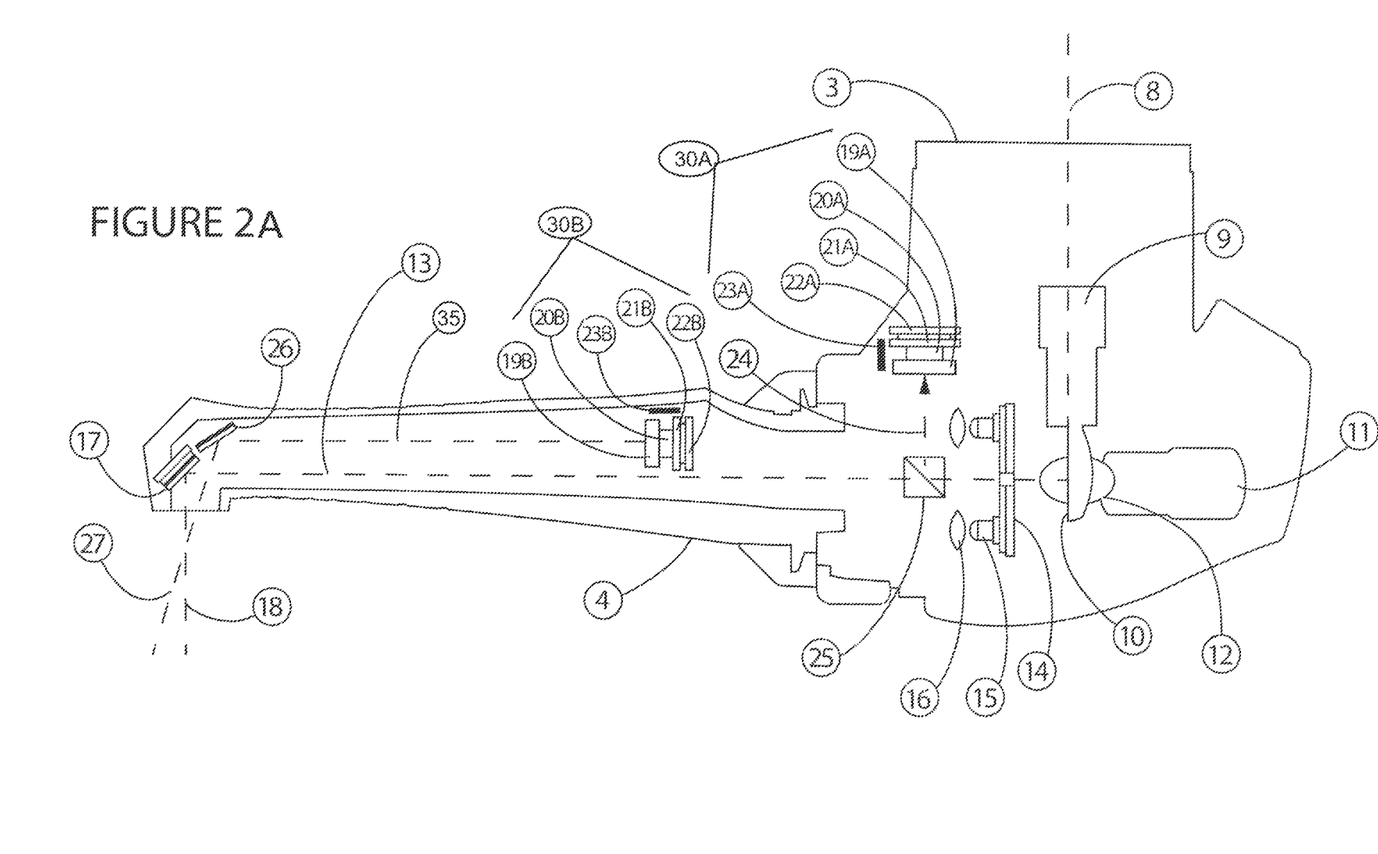
FIGS. 2A-2C depict dental systems for scanning and treatment according to different embodiments.

With reference to FIG. 2A, in one embodiment, a main chamber 3 of a dental laser system houses an X Galvo 9 and a Y Galvo 11, and associated reflective mirrors 10, 12 that are mounted on the X and Y galvanometers, respectively. The laser beam enters the module approximately along axis 8, reflects off the respective reflective mirrors 10, 12 of X Galvo 9 and Y Galvo 11, is redirected through the hand piece 4 substantially along axis 13, reflects off turning mirror 17, and exits the hand piece substantially along axis 18. In this embodiment, a camera assembly 30A, which includes an image sensor 22A, a filter 21A, a fluidic lens 20A, a lens stack 19A, and a focusing motor 23A, is mounted within the main chamber 3. The camera assembly 30A can receive a beam of light split by a beam splitter 25. The beam splitter 25 can transmit therethrough the treatment laser beam and, optionally, a marking laser beam, substantially along the optical axis 13.

An optical device 14 can emit light from a light source 15 through a lens 16, non-collinearly but in parallel to the optical axis 13. The emitted light can reflect off the turning mirror 17, and may be emitted through the tip of the hand piece 4, with a waist around the optical axis 18, towards a treatment area. Alternatively, the illumination light source can be coupled into a light guide and be emitted towards the turning mirror 17 in a hand piece, so that the illumination light is directed to the treatment area. Light reflected from the treatment area representing a visible image thereof may propagate substantially along the hand piece axis 18, reflect off turning mirror 17, propagate substantially along the optical axis 13, and may be reflected off the beam splitter 25 along an optical axis 24 into the image sensor 22A. As the laser beam and the light reflected from the treatment area both travel along the axis 13, the camera assembly 30A may be referred to as "on-axis" camera assembly.

In addition, a camera assembly 30B that includes an image sensor 22B is also located in the hand piece 4, along with a filter 21B, a fluidic lens 20B, a lens stack 19B, and a focusing motor 23B. The image sensor 22B can be mounted such that light reflected from the area of treatment entering the hand piece 4 along the optical axis 27 and reflecting off a turning mirror 26 can propagate along axis 35 to the image sensor 22B. In one embodiment, the optical axis 27 is at an angle of about 15° relative to the axis 18. In general, the angle between the two axes 18, 27 can be within a range from about 5° up to about 45°. No significant portion of the light received at the camera assembly 30B travels along any of the axes along which the laser beam propagates, e.g., the axes 13, 18. Therefore, the camera assembly 30B may be referred to as "off-axis" camera assembly. In each camera assembly 30A, 30B, various components, namely, the filter, fluidic lens, lens stack, and focusing motor are optional. Different embodiments of a camera assembly can include none, any one, or a combination of any two or more of these components.

Figure 2B:
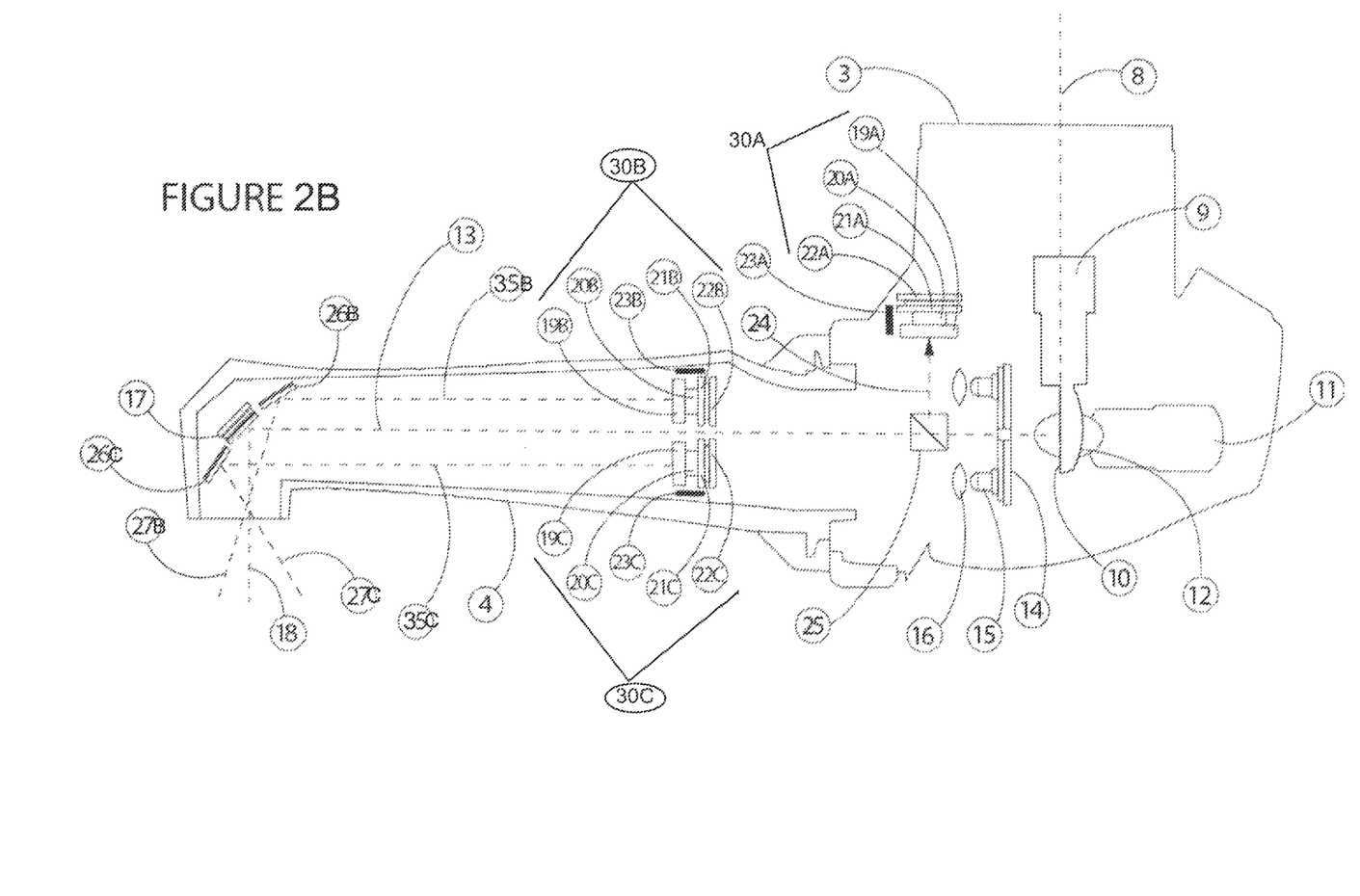
Figure 2C:
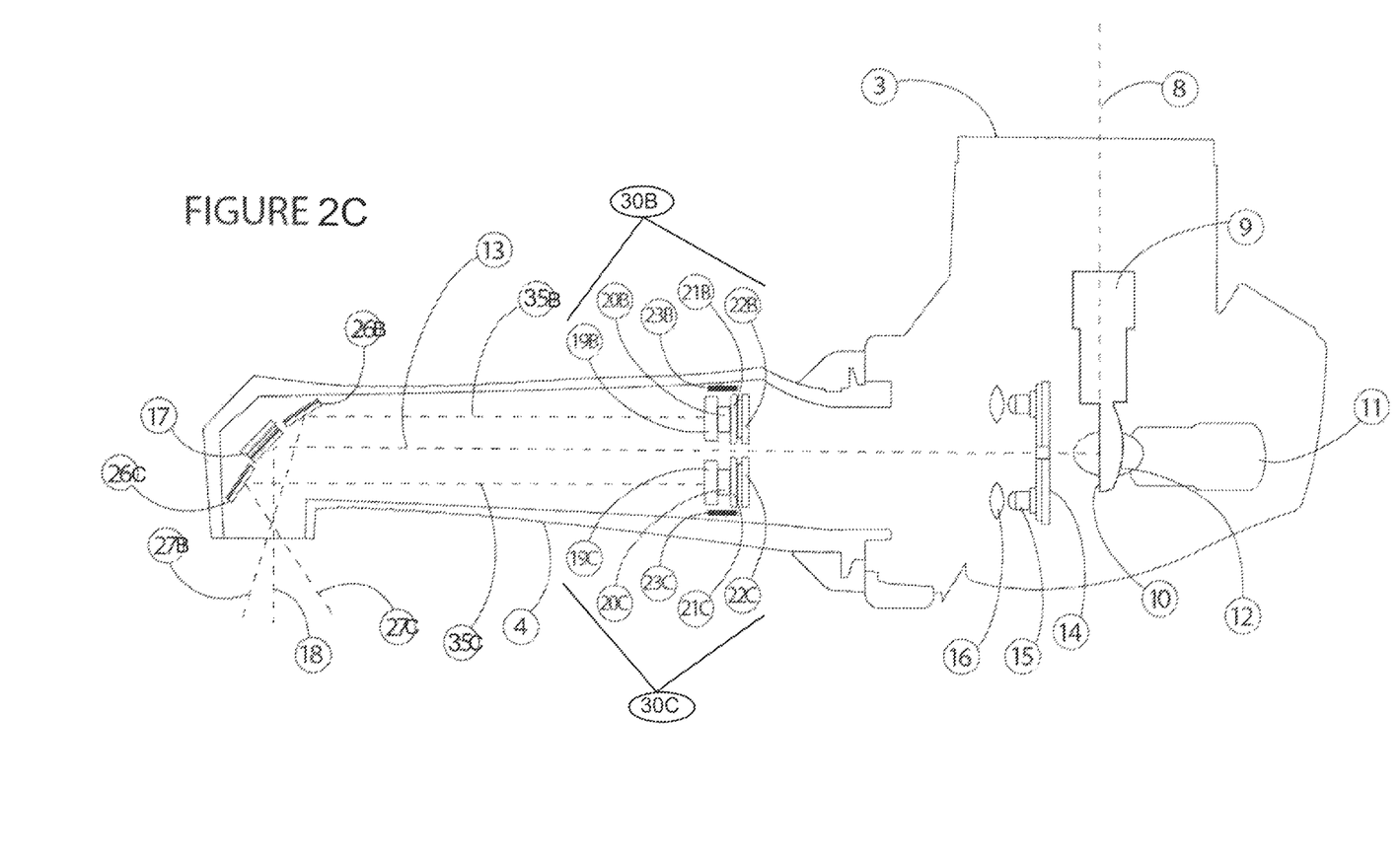

Though FIG. 2A shows two camera assemblies 30A, 30B, i.e., imaging systems, it should be understood that this is for illustrative purposes only. Various embodiments may include only the camera assembly 30A or only the camera assembly 30B. Some embodiments include two or more off-axis camera assemblies. For example, with reference to FIG. 2B, one embodiment includes two off-axis camera assemblies 30B, 30C in addition to the on-axis cameral assembly 30A. With reference to FIG. 2C, another embodiment does not include the on-axis camera assembly 30A but include two off-axis camera assemblies 30B, 30C. More than two off-axis camera assemblies may also be included. Each of the camera assemblies 30B, 30C is positioned at different locations in the hand piece 4. Either or both of these assemblies can also be located in the main chamber 3. The camera assembly 30B receives light reflected off mirror 26B, impinging thereon along axis 27B, and the camera assembly 30C receives light reflected off mirror 26C, impinging thereon along axis 27C. The axes 27B, 27C are at an angle relative to each other and are at different angles, respectively, relative to the optical axis 18. In some embodiments, both off-axis camera assemblies 30B, 30C may receive light reflected off one mirror, e.g., mirror 26B or mirror 26C, but impinging thereon along different axes that are at different angles relative to each other and to the optical axis 18. The images obtained from two or more camera assemblies can be analyzed to accurately determine the depth of the corresponding image slices.

Figure 3:
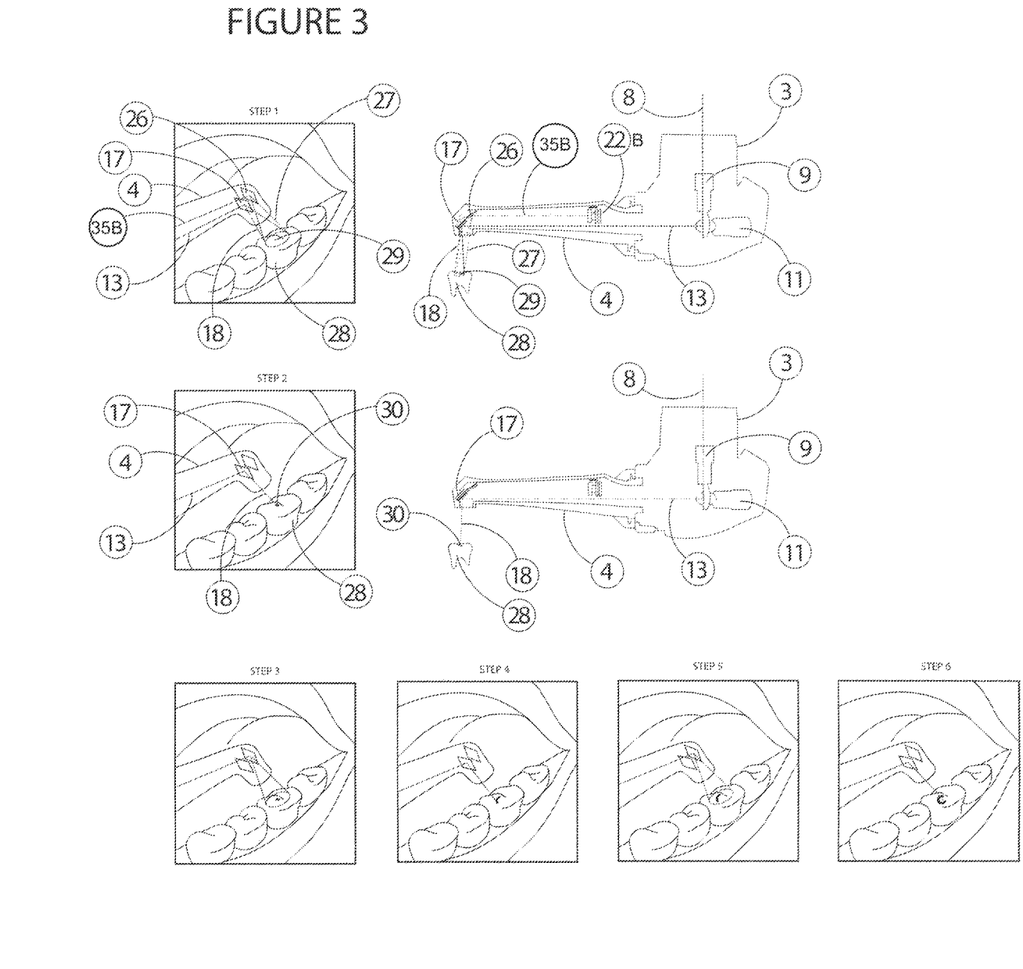
FIG. 3 illustrates an exemplary alternate scanning and ablation procedure in which scanning is performed using structured light, according to one embodiment.

FIG. 3 illustrates an exemplary treatment process in which ablation and measurement/scanning using structured light are performed alternately. The galvanometers 9 and 11 are housed in the main chamber 3 and can direct visible light for measurement (and far infrared light, e.g., a laser beam, for ablation), received along optical axis 8, towards the tissue to be treated. The visible light is reflected off the galvanometer mirrors that are used to direct the ablation laser during treatment, and may propagate substantially along the optical axis 13, reflect off the turning mirror 17, and then exit the hand piece 4 along the optical axis 18. The hand piece 4 houses an image sensor 22B which can receive images of the tissue being treated. In particular, light reflected from the tissue can enter the hand piece 4 along an optical axis 27, reflect off a tuning mirror 26, and can be received by the sensor 22B along the axis 35B, which is substantially parallel to the optical axis 13. Step 1 illustrates a movement of the galvanometers 9, 11 to direct visible light onto a tooth 28 in an ovular region 29. As the visible light is scanned by galvanometers 9, 11 the light reflecting from the tooth surface can be captured by the image sensor 22B, as described above. Using the captured images, a contour of the scanned tooth surface can be determined.

Step 2 shows the ablation laser reflecting off the turning mirror 17, propagating along the optical axis 18, and ablating a portion of the tooth 28 in a pattern 30. Step 3 shows the structured (i.e., scanned) visible light being directed again to the tooth 28. In this step, the laser system can be turned off so that the ablation laser beam is not directed to the area to be treated. In step 3, the image sensor 22B can measure the contour of the treatment area, including the of the surface of the tooth 28, that was at least partially treated according to the ablation pattern 30 after the ablation in step 2. Step 4 shows the ablation laser being reactivated and ablating an additional portion of the tooth 28. In step 5, the ablation laser is turned off and a new measurement is obtained after the ablation in step 4. Ablation can continue in step 6 and, in general, the treatment process that includes alternating ablation/contour determination steps is continued until a selected treatment is completed.

In one embodiment, during scanning, the galvanometer mirrors may rotate into a "park" position not used during laser ablation, and may flutter, i.e., move in a controlled manner. This can cause the structured light to be directed to the dental treatment area within a selected shape (circle, oval, rectangle, etc.) according to a specified scanning pattern such as a zig-zag pattern, spiral pattern, etc., to scan the treatment area (e.g., a surface of a tooth) with the controlled illumination.

Figure 4:
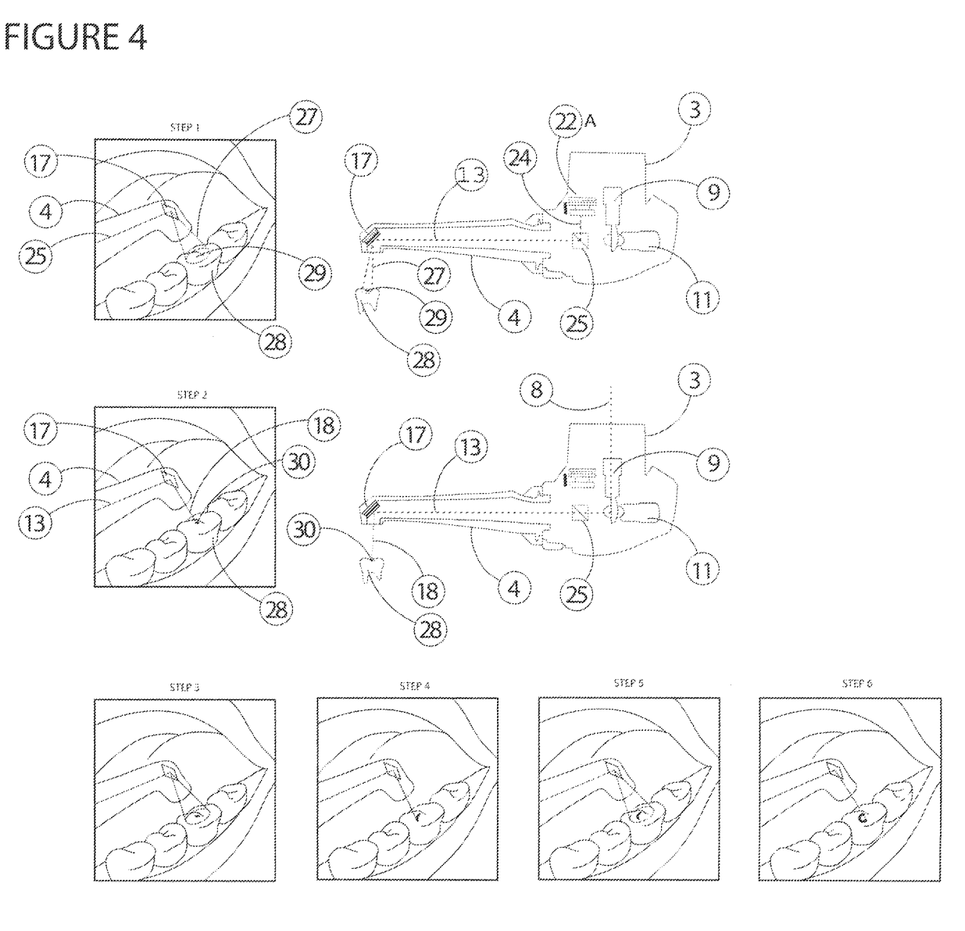
FIG. 4 illustrates another exemplary alternate scanning and ablation procedure in which scanning is performed using focus adjustment, according to one embodiment.

FIG. 4 illustrates another embodiment of a treatment process that includes the alternating ablation and measurement steps, using focus adjustment and recognition for the optical measurements. Scanning is not required in an adjustable focal length system. In this embodiment, ablation is performed using a laser beam guided by galvanometers, and the 2D measurement is performed using an "on-axis" camera with adjustable focus. On-axis generally means at least partial propagation of the light used to capture images and at least partial propagation of the light reflected from the treatment region that may represent an image thereof occur substantially along a common axis, e.g., the optical axis 13.

In step 1, an image sensor 22A can image the tooth 28 using light reflected from a treatment area and received via an optical axis 18, reflected over the turning mirror 17, propagating substantially along the optical axis 13, and being redirected by the beam splitter 25 substantially along the axis 24. Alternatively or in addition, in some embodiments, with reference to FIG. 3, the sensor 22B can image the tooth 28 using light reflected from a treatment area and received via the optical axis 27, reflected over the turning mirror 26, and propagating substantially along the optical axis 35B. Referring again to FIG. 4, in step 2 the ablation laser is activated and the ablation laser beam travels along an optical axis 13, reflecting off the turning mirror 17, and emitting from the hand piece 4 along the optical axis 18. The laser beam may ablate a portion of the tooth 28 within an area of treatment according to the pattern 30.

Step 3 shows the sensor 22A imaging the surface of the tooth 28 after the ablation in step 2. In step 3, the laser beam is turned off. Steps 4 and 6 illustrate that the ablation laser is reactivated and, as such, the ablation region 30 can get larger. In step 5, the laser beam is turned off and a measurement is obtained after the ablation in step 4. This treatment process including alternating measurement and ablation steps can continue until a selected treatment is completed.

One advantage of the on-axis imaging system is that the operator can align the system for imaging and measurement, and can then easily switch over to laser ablation without moving the hand piece. Various embodiment of a 3D measurement/scanning system may include an imaging device such as a CMOS chip, coupled to a lens stack that is mounted to a motor shaft, so that a short depth of focus can be achieved. The motor may include both a controller and amplifier, and the lens stack motor control can be linked to the system processor. By controlling the lens stack motor position through a central control system, the image can be focused, or moved automatically or remotely using a hand joystick or the foot pedal, or another input device. A foot pedal is illustrative only; the control of any parameter described below can be achieved using any suitable input device such as a mouse, keyboard, joy stick, touch screen panel, a slider switch, etc.

The motor and lens stack allow for the shortest depth of focus position of the image sensor to be adjusted as the tooth ablation continues so that a number of image slices, e.g., images at gradually increasing depths, can be captured. Once the images are obtained, a digital file including those images can be processed using hardware and/or software components so as to determine the portion of the captured images that is in focus. Based on such determination, a depth of each slice can be determined, and a contour of the dental treatment region for each image slice can be computed using the corresponding depth. Depth determination can also account for any unintentional movement of the hand piece, such as jitter.

Figure 5:
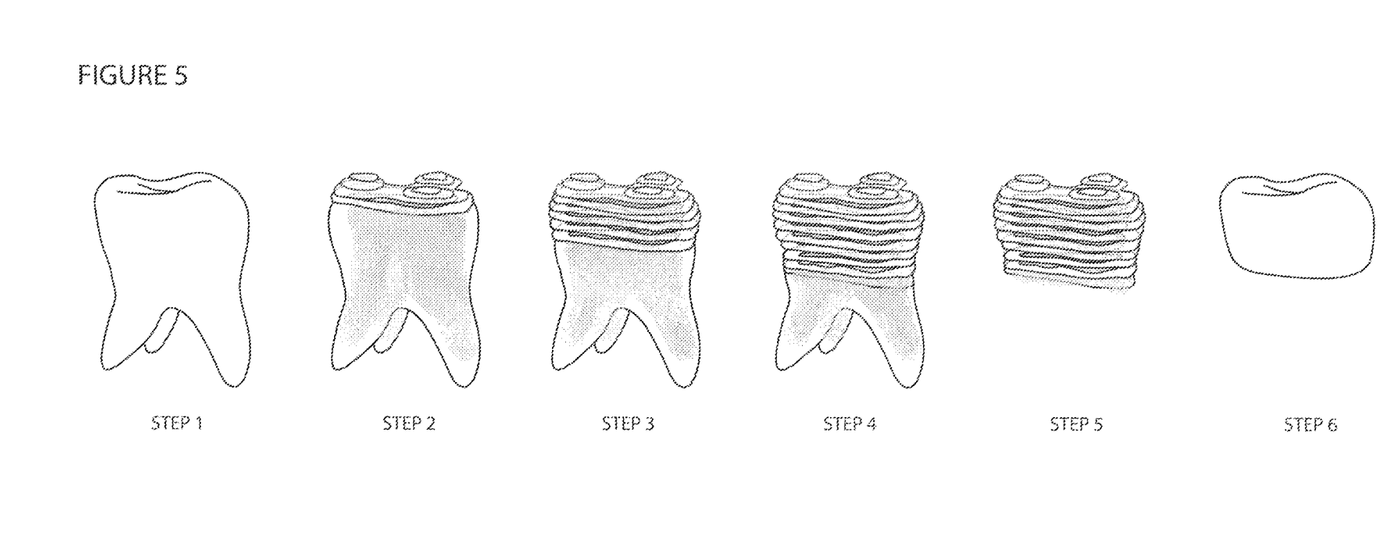
FIG. 5 illustrates an exemplary alternate scanning and ablation procedure to obtain a number of two-dimensional (2D) contours and reconstruction of a three-dimensional (3D) model based thereon, according to one embodiment.

FIG. 5 shows an exemplary treatment process including alternating scanning (i.e., contour determination) and ablation steps, and the creation of a final restoration digital model. Specifically, step 1 depicts an untreated tooth. Step 2 illustrates four iterations of the alternating procedure. In each iteration, a substantially two-dimensional (2D) image measurement, i.e., contour determination of the tooth, is followed by ablation. As the tooth is ablated, the 2D image slices and the corresponding contours 502-508 that are determined by analyzing the captured images are digitally stored. As these slices represent ablated tissue, they are not actually present on the tooth after the ablation.

Step 3 illustrates a total of eight substantially 2D image slices 502-516, and step 4 illustrates twelve substantially 2D image slices 502-524. Step 5 illustrates that the twelve digital 2D image slices 502-524 obtained from steps 2-4 can be digitally combined to create a solid 3D representation (e.g., as a digital image) of the tissue that was ablated and needs to be replaced, as depicted in step 6. It should be understood that a restoration that includes 12 scans is illustrative only and, in general, a restoration can include fewer (e.g., 2, 3, 4, etc.) or many more (e.g., 50, 100, 200 etc.) scans.

One advantage of the various embodiments of the integrated scanning and ablation system is that the restoration can be more accurate and is more likely to resemble the original tooth, relative to conventional techniques. This is because in conventional techniques, images are typically taken before and after the treatment only, because taking additional images during the treatment can be cumbersome and/or potentially harmful to a person being treated, as the operator would need to frequently switch between the ablation and scanning systems. Moreover, conventional scanning and laser-based ablation systems cannot be readily integrated, because these systems include optical subsystems that are generally incompatible with each other.

In some embodiments described herein, optical subsystems of the ablation system, such as the galvo-controlled mirrors, are adapted for scanning as well. Additionally, or in the alternative, the scanning and ablation systems may use different optical components, such as separate turning mirrors 17, 26 (shown in FIG. 2A). In various embodiments, the particular geometries of these components, such as their positions, relative angles, etc., are used in analyzing the scanned images so as to determine contours of the treated region. This can enable obtaining a number of intermediate slices (e.g., 10, 50, 100, or more) during the treatment in addition to the images captured before and after the treatment, without having to swap in and out the scanning and ablation/treatment systems. The depth of two consecutive slices can be small (e.g., 0.02 mm, 0.05 mm, 0.1 mm, 0.5 mm, etc.), relative to the total depth of a cut during a treatment, which can be up to about 1 cm or even more. A contour at each slice can be a substantially two-dimensional contour, and a 3D image can be constructed using the 2D contours, as depicted in steps 5 and 6 of FIG. 5.

As the slices obtained during treatment correspond to small changes in depth (i.e., the distance between two consecutively imaged surfaces) relative to the change in depth associated with the images before and after the treatment, in various embodiments described herein only a small degree of interpolation is necessary to determine the shape of the removed tissue from one imaged contour to the next imaged contour. This can simplify the processing and/or increase accuracy thereof. Moreover, the images can be obtained while a single hand piece, facilitating both treatment and imaging, is held in a patient's mouth. Therefore, the inaccuracies related to a lack of orientation information and reference can be avoided or mitigated.

In some embodiments, the processor generating the 3D model using the 2D contours determines the depths of the slices corresponding to those contours by analyzing some or all of the contours and/or some or all of the images corresponding to those contours. This analysis can compensate for any unintentional movement of the hand piece (e.g., jitter) during treatment and/or scanning. Based on the parameters set by the operator, the main system computer/processor can estimate the depth of cut from each treatment step. As the 2D contours are determined from tissue scans that are interleaved between different treatment steps, the processor may use the estimated depths of one or more of the previously performed treatment steps in accurately determining the 2D contour of an image obtained in a particular scan. The processor may also use the estimated depths in the reconstruction of the 3D model, thereby increasing the accuracy thereof.

In various embodiments, using the user interface 5 (depicted in FIG. 1), a wide array of hard and soft tissue procedures can be employed. By way of example and without limitation, an operator may insert the hand piece 4 into the patient's mouth and observe the image of the hard or soft tissue on the user interface 5 or another monitor. While viewing the tooth, the hand piece 4 may be specifically positioned to view an area of interest, such as an area to be treated. The laser beam guidance system can be used to scan the dental treatment area according to a pattern of light and/or may be used to guide the laser beam during treatment. Using the contours generated during alternating scanning and treatment steps, a three dimensional (3D) model of portions of the tissue removed from the dental treatment area can be created. Based on the 3D model, a restoration can be created and applied to the treated dental area. Optionally, the 3D model can be modified prior to creating the restoration. The modification can be beneficial if the portion of the tissue removed included defects such as a lost part, e.g., due to a chipped tooth, or was deficient in any respect. These defects and deficiencies can be eliminated or reduced using the optional modification. Any of a variety of 3D modeling tools and systems can be employed, including haptic-based interactive modeling systems to modify the model, prior to manufacture of the replacement piece or restoration.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. An integrated device for both determining a contour of a dental treatment area and ablating at least a portion of the dental treatment area, the integrated device comprising:
   a laser source for generating an ablation laser beam;
   a laser beam guidance system for guiding, via a handpiece held by an operator, the ablation laser beam to the dental treatment area to ablate at least a portion of the dental treatment area;
   an imaging system to obtain, via the handpiece held by the operator, an image of the dental treatment area based on light rays reflected therefrom;
   a control system to perform operations comprising:
      (a) generating a first contour of the dental treatment area based on a first image received at the imaging system;
      (b) generating a second contour of the dental treatment area based on a second image received at the imaging system after ablation of at least a portion of the dental treatment area; and
      (c) repeating steps (a) and (b) to generate additional contours until treatment is completed; and
   a processor to generate a three dimensional (3D) model of portions of tissue removed from the dental treatment area using the generated contours.

2. The device of claim 1, wherein the imaging system comprises an adjustable focus lens.

3. The device of claim 2, further comprising at least one of a joystick and a foot pedal for adjusting a focal length of the adjustable focus lens.

4. The device of claim 2, wherein the adjustable focus lens comprises at least one of a motorized lens stack and a liquid lens.

5. The device of claim 1, wherein the control system is adapted for determining an in-focus portion of the image.

6. The device of claim 1, wherein the control system is adapted for determining the first contour and the second contour based at least in part on a geometry of at least one of a component of the laser beam guidance system and the imaging system.

7. The device of claim 1, wherein both the ablation laser beam and the light rays reflected from the dental treatment area travel along a common optical axis.

8. The device of claim 7, further comprising a splitter for directing the light rays reflected from the dental treatment area to the imaging system.

9. The device of claim 1, wherein the imaging system is located within the handpiece.

10. The device of claim 1, wherein the ablation laser beam is guided to the dental treatment area along a first axis and light rays reflected from the dental treatment area travel along a second axis that is at an angle with respect to the first axis.

11. The system of claim 1, further comprising an illumination system for providing light to the dental treatment area.

12. The system of claim 11, wherein the illumination system is adapted for providing light having a pattern.

13. The system of claim 12, wherein the pattern comprises at least one of a spot, a one-dimensional pattern, and a two-dimensional pattern.

14. The system of claim 11, wherein the laser beam guidance system is adapted to scan the dental treatment area by directing light from the illumination system.

15. A method of determining a contour of a dental treatment area and ablating at least a portion of the dental treatment area, the method comprising the steps of:
   (a) receiving at an imaging system a first image based on a first set of light rays reflected from a dental treatment area and traveling via a handpiece;
   (b) generating a first contour of the dental treatment area based on the first image;
   (c) directing via the handpiece an ablation laser beam to the dental treatment area using a laser beam guidance system, to remove at least a portion of tissue from the dental treatment area;
   (d) after removing at least a portion of tissue from the dental treatment area, receiving at the imaging system a second image based on a second set of light rays reflected from the dental treatment area and traveling via the handpiece;
   (e) generating a second contour of the dental treatment area based on the second image;
   (f) repeating steps (c) through (e) to generate additional contours until treatment is completed; and
   (g) using the generated contours to generate a three dimensional (3D) model of portions of tissue removed from the dental treatment area.

16. The method of claim 15, wherein at least one of the first contour and the second contour is a two-dimensional (2D) contour.

17. The method of claim 15, wherein:
   receiving the first image comprises adjusting a focal length associated with the imaging system; and
   generating the first contour comprises determining an in-focus portion of the first image.

18. The method of claim 15, wherein the focal length is adjusted using at least one of a joy stick and a foot pedal.

19. The method of claim 15, wherein both the ablation laser beam and the first and second sets of light rays reflected from the dental treatment area and received by the imaging system travel along a common optical axis.

20. The method of claim 15, wherein receiving the first image comprises scanning the dental treatment area according to a pattern of light obtained from an illumination system.

21. The method of claim 20, wherein the ablation laser beam is guided to the dental treatment area along a first axis and the first and second sets of light rays reflected from the dental treatment area and received by the imaging system travel along a second axis that is at an angle with respect to the first axis.

22. The method of claim 20, wherein the pattern comprises at least one of a spot, a one-dimensional pattern, and a two-dimensional pattern.

23. The method of claim 20, further comprising controlling the laser beam guidance system to scan the dental treatment area according to the pattern of light.

24. The method of claim 15, further comprising creating a restoration using the 3D model.

25. The method of claim 24, further comprising modifying the 3D model prior to creating the restoration.

26. The method of claim 24, further comprising applying the restoration to the dental treatment area.

* * * * *